United States Patent
Agee

(10) Patent No.: US 10,815,165 B1
(45) Date of Patent: Oct. 27, 2020

(54) PRODUCTION OF BASESTOCKS FROM PARAFFINIC HYDROCARBONS

(71) Applicant: Emerging Fuels Technology, Inc., Tulsa, OK (US)

(72) Inventor: Kenneth L. Agee, Tulsa, OK (US)

(73) Assignee: EMERGING FUELS TECHNOLOGY, INC., Tulsa, OK (US)

( * ) Notice: Subject to any disclaimer, the term of this patent is extended or adjusted under 35 U.S.C. 154(b) by 0 days.

(21) Appl. No.: 15/991,379

(22) Filed: May 29, 2018

Related U.S. Application Data

(63) Continuation-in-part of application No. 15/602,308, filed on May 23, 2017, now abandoned.
(Continued)

(51) Int. Cl.
*C07C 2/12* (2006.01)
*C10G 3/00* (2006.01)
(Continued)

(52) U.S. Cl.
CPC .................. *C07C 2/12* (2013.01); *C10G 3/40* (2013.01); *C10G 3/50* (2013.01); *C10G 7/003* (2013.01); *C10G 9/00* (2013.01); *C10G 50/00* (2013.01); *C10G 69/126* (2013.01); *C10M 107/04* (2013.01); *C10M 107/10* (2013.01);
(Continued)

(58) Field of Classification Search
None
See application file for complete search history.

(56) References Cited

U.S. PATENT DOCUMENTS

| 4,520,221 A * | 5/1985 | Hsia Chen | B01J 29/40 585/517 |
| 4,658,079 A * | 4/1987 | Chen | B01J 29/40 585/517 |

(Continued)

OTHER PUBLICATIONS

Chiappero, Martina et al. "Direct conversion of triglycerides to olefins and paraffins over noble metal supported catalysts", Fuel, 2011, vol. 90, No. 3, pp. 1155-1165.
(Continued)

*Primary Examiner* — In Suk C Bullock
*Assistant Examiner* — Alyssa L Cepluch
(74) *Attorney, Agent, or Firm* — Head, Johnson, Kachigian & Wilkinson, PC

(57) ABSTRACT

A process to convert paraffinic feedstocks into renewable poly-alpha-olefins (PAO) basestocks. In a preferred embodiment of the invention, renewable feed comprising triglycerides and/or free fatty acids are hydrotreated producing an intermediate paraffin feedstock. This paraffin feedstock is thermally cracked into a mixture of olefins and paraffins comprising linear alpha olefins. The olefins are separated and the un-reacted paraffins are recycled to the thermal cracker. Light olefins preferably are oligomerized with a surface deactivated zeolite producing a mixture of slightly branched oligomers comprising internal olefins. The heavier olefins (C8-C14) are oligomerized, preferably with a BF3 catalyst and co-catalyst to produce PAO products. The oligomerized products can be hydrotreated and distilled together or separate to produce finished products that include naphtha, distillate, solvents, drilling fluid, and PAO lube basestocks.

25 Claims, 4 Drawing Sheets

Related U.S. Application Data

(60) Provisional application No. 62/340,241, filed on May 23, 2016.

(51) Int. Cl.
| | |
|---|---|
| *C10G 7/00* | (2006.01) |
| *C10G 50/00* | (2006.01) |
| *C10G 9/00* | (2006.01) |
| *C10G 69/12* | (2006.01) |
| *C10M 107/04* | (2006.01) |
| *C10M 107/10* | (2006.01) |
| *B01J 29/40* | (2006.01) |
| *B01J 29/70* | (2006.01) |
| *B01J 27/10* | (2006.01) |
| *B01J 27/12* | (2006.01) |
| *C10N 70/00* | (2006.01) |

(52) U.S. Cl.
CPC ............... *B01J 27/10* (2013.01); *B01J 27/12* (2013.01); *B01J 29/40* (2013.01); *B01J 29/703* (2013.01); *B01J 29/7046* (2013.01); *C10G 2300/1085* (2013.01); *C10G 2300/1092* (2013.01); *C10G 2400/22* (2013.01); *C10M 2205/0225* (2013.01); *C10N 2070/00* (2013.01)

(56) References Cited

U.S. PATENT DOCUMENTS

| | | |
|---|---|---|
| 4,678,645 A | 7/1987 | Chang et al. |
| 4,982,031 A | 1/1991 | Chen |
| 5,000,840 A | 3/1991 | Anthes et al. |
| 5,136,118 A | 8/1992 | Buchanan et al. |
| 5,146,022 A | 9/1992 | Buchanan et al. |
| 5,243,112 A * | 9/1993 | Chester .............. C07C 2/12 585/12 |
| 5,602,086 A * | 2/1997 | Le .............. C10M 111/04 508/591 |
| 5,744,677 A | 4/1998 | Wu |
| 6,497,812 B1 | 12/2002 | Schinski |
| 8,440,872 B2 | 5/2013 | Buchanan et al. |
| 2001/0004972 A1 | 6/2001 | Miller et al. |
| 2006/0211904 A1* | 9/2006 | Goze .............. C07C 2/20 585/520 |
| 2007/0135665 A1 | 6/2007 | Wiese et al. |
| 2010/0292424 A1 | 11/2010 | Wu et al. |
| 2011/0288256 A1* | 11/2011 | Vermeiren .............. C07C 11/08 526/348.6 |
| 2012/0108871 A1* | 5/2012 | Miller .............. C10G 3/46 585/310 |
| 2013/0303818 A1* | 11/2013 | Inagaki .............. C07C 2/34 585/511 |
| 2014/0163249 A1 | 6/2014 | Chen et al. |
| 2014/0243565 A1 | 8/2014 | Week |

OTHER PUBLICATIONS

Lee, Dong Wook; International Search Report and Written Opinion dated Aug. 9, 2017; Korean Intellectual Property Office.

* cited by examiner

PRODUCTION OF BASESTOCKS FROM PARAFFINIC HYDROCARBONS

CROSS-REFERENCE TO RELATED APPLICATIONS

This application claims priority to and the benefit of U.S. patent application Ser. No. 15/602,308, filed May 23, 2017, and U.S. Provisional Patent Application Ser. No. 62/340,241, filed May 23, 2016, which are herein incorporated in their entirety by reference.

BACKGROUND OF THE INVENTION

Field of the Invention

The present invention relates to a process and system to produce solvents, fuels, and Group III and Group IV basestocks from paraffinic hydrocarbons. Such paraffinic hydrocarbons can be produced, for example, by a Fischer Tropsch process or can be produced by hydroprocessing a renewable feedstock, such as fats and oils comprising triglycerides free fatty acids, or mixtures thereof. Hydroprocessing may include hydrodeoxygenation, decarboxylation, and saturation, and will be referred to herein as hydrodeoxygenation.

2. Description of the Related Art

Fischer Tropsch syncrude, preferably syncrude made by a non-shifting Fischer Tropsch catalyst, comprises predominately normal paraffins (n-paraffins) also referred to as straight chain hydrocarbons. While the Fischer Tropsch synthesis, preferably with a non-shifting Fischer Tropsch catalyst, produces a broad range of carbon distribution from C1 to approximately C100, it produces, however, a small range of variation in molecular structure. Such molecules are predominately straight chain paraffins with lesser amounts of alpha olefins and primary alcohols. The alpha olefins and primary alcohols can easily be saturated yielding a range of high purity n-paraffins. Naturally occurring triglycerides, including fatty acids, can be hydroprocessed to produce predominately paraffin hydrocarbons of narrow boiling range.

The prior art teaches that these high purity n-paraffin molecules can be refined into paraffin solvents, oils, and waxes. The waxes can also be hydroisomerized into high quality iso-paraffin oils and basestocks. Such high quality basestocks are referred to in the market as Group III basestocks. The Group III designation is a formal industry term. The American Petroleum Institute designates lubricant base oils as follows: Group I, Group II, Group III and Group IV. As the quality of the basestock that can be produced from a high purity Fischer Tropsch wax often exceeds the quality of a typical Group III basestock, the basestock produced by hydroisomerization of Fischer Tropsch waxes may be known in the market by the informal term Group III+. These basestocks are highly desirable products and therefore represent one of the highest value products that can be produced by a Fischer Tropsch process.

As known to those skilled in the art, the hydroisomerization of Fischer Tropsch waxes to produce Group III or Group III+ basestocks will result in cracking a portion of the wax to lighter (lower molecular weight, lower carbon number) iso-paraffinic products, too light to be included in the Group III basestock products. Such light products may be further processed and finished as solvents, distillates such as jet or diesel, or drilling fluids.

Another desirable group of products in the market are known as Group IV basestocks. Group IV basestocks are made by oligomerization of linear alpha olefins. These linear alpha olefins are commercially produced by oligomerization of ethylene to even number higher olefins. Most commercial Group IV basestocks (also known as polyalphaolefins or PAO) are made by oligomerization of 1-decene, which is a small fraction of the products of ethylene oligomerization.

Historically, alpha olefins have also been made by thermally cracking petroleum waxes. Such thermal cracking of petroleum waxes will yield a distribution of alpha olefins with a substantial portion (even and odd) in the C6 to C16 range. In U.S. Pat. Nos. 5,136,118 and 5,146,022, a process is demonstrated whereby petroleum waxes are thermally cracked into alpha olefins. The C6 to C16 olefins are further oligomerized into Group IV basestocks with properties similar to basestocks made from 1-decene. Some prior art processes, such as U.S. Pat. No. 8,440,872, have proposed a process that will convert a narrow fraction of a Fischer Tropsch syncrude into Group IV basestocks.

It is an objective of the present invention to convert a broad range of paraffin feedstocks into Group III and Group IV basestocks. When the paraffin source is from a Fischer Tropsch reaction, it is an objective to provide a process that will convert a major portion of a Fischer Tropsch syncrude into Group III and Group IV basestocks.

SUMMARY OF THE INVENTION

The present invention is a process designed to produce high yields of Group III and Group IV basestocks from paraffinic hydrocarbons, such as a Fischer Tropsch syncrude product, and/or from renewable feedstocks comprising triglycerides, diglycerides, monoglycerides, and free fatty acids. Heavy waxy Fischer Tropsch components are hydroisomerized, hydrotreated and distilled into one or more Group III basestock cuts. Lighter Fischer Tropsch molecules and/or certain renewable feedstocks (after hydrodeoxygenation) are saturated to n-paraffins and then thermally cracked to produce a mixture of alpha olefins. Optionally, the very heavy C50+ waxy Fischer Tropsch components are not hydroisomerized but are also cracked to produce a mixture of olefins preferably in the C8 to C14 range. The target range (C8-C14) of olefins produced in the process are oligomerized, hydrogenated, and fractionated to produce Group IV basestocks. This oligomerization step is referred to herein as the primary oligomerization. Light olefins are dimerized, trimerized and/or preferably oligomerized by various means, including ethylene oligomerization and oligomerization over a surface deactivated zeolite catalyst. A small portion of the light thermally cracked olefins may also be subjected to hydroformylation to alcohols and used as a co-catalyst in the primary oligomerization step.

Therefore, the process makes it possible to convert light olefins (C2-C7) including even and odd carbon numbers from thermal cracking into intermediate products (even number alpha olefins and higher slightly branched internal olefins) useful to increase the yields of the target products of the process. Olefins can also optionally be used to alkylate an imported aromatic feedstock to make a polar aprotic blendstock useful for blending with Group III and Group IV basestocks of the present invention. Additionally, a minor portion of the olefins produced by thermal cracking may optionally be used to make a viscosity index (VI) improver.

DETAILED DESCRIPTION OF THE INVENTION

Figure 1:
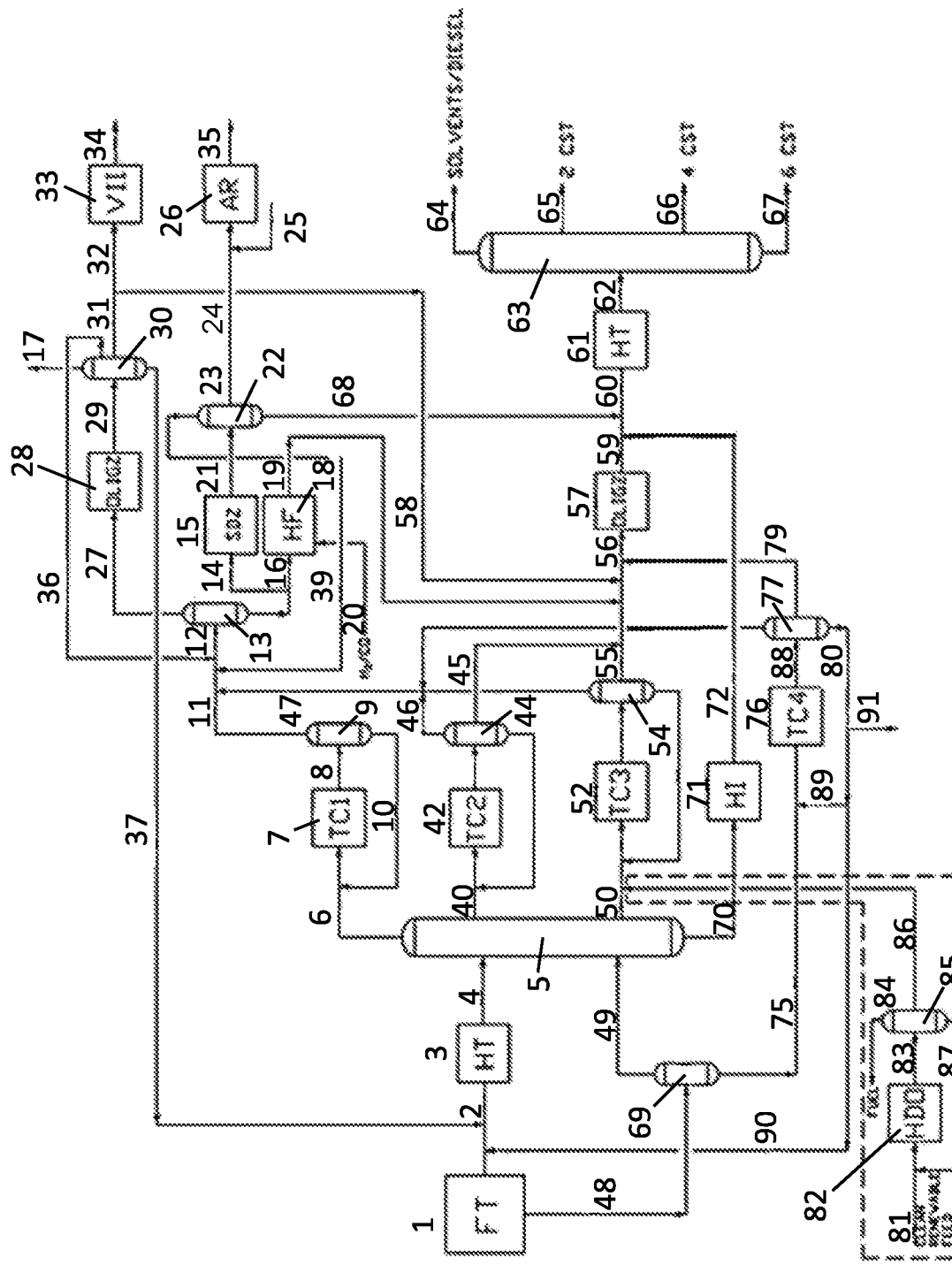
FIG. 1 is a simplified process flow diagram showing the major components of a process and system according to a first preferred embodiment of the present invention.

The embodiments discussed herein are merely illustrative of specific manners in which to make and use the invention and are not to be interpreted as limiting the scope of the invention. It is an objective of the present invention to make solvents and fuels including diesel and renewable diesel and both Group III and Group IV basestocks in high yield from paraffinic feedstocks such as a Fischer Tropsch syncrude and/or hydrodeoxygenating a renewable feed such as fats and oils containing triglycerides or fatty acids. Group III basestocks of the present invention are made by hydroisomerization of heavy waxy paraffins, such as Fischer Tropsch wax components. Fischer Tropsch wax may be defined as the C20+ fraction of the Fischer Tropsch syncrude product. In the present invention, all or a portion of the Fischer Tropsch wax may be used to produce Group III basestocks by hydroisomerization. Other fractions of the Fischer Tropsch syncrude and/or the hydrodeoxygenated renewable feed may be thermally cracked to make alpha olefins that can be converted to solvents, fuels including renewable diesel, and Group IV basestocks. If it is desirable to produce more Group IV basestocks, some or all of the Fischer Tropsch products may be separated by distillation, fractional crystallization, segmentation or any other separation process known to one skilled in the art and used as feed to one or more thermal crackers to produce additional alpha olefins which can be oligomerized to Group IV basestocks.

Waxy components not used for hydroisomerization and all or a part of the remaining lighter Fischer Tropsch fractions and/or any renewable materials, including triglycerides and fatty acids (after hydrodeoxygenation), are used as feed to one or more thermal crackers to make olefins (including even and odd carbon number) for oligomerization to solvents and fuels including renewable diesel and Group IV basestocks. The resulting paraffinic intermediate products (either Fischer Tropsch derived or renewable) can be thermally cracked with good selectivity to linear alpha olefins. The resulting olefins will range from C2 to C20 or higher (including even and odd carbon number). Most commercial oligomerization processes designed to make Group IV basestocks start with 1-decene or a mixture of even carbon number olefins with a narrow distribution centered around 1-decene. The process of the present invention uses one or more thermal crackers to make a range of predominately linear alpha olefins comprising even and odd number olefins. The range of alpha olefins that are used for oligomerization to Group IV basestocks can be tailored to meet the requirements of the finished products. As such, olefins that are too heavy can be recycled to be hydrotreated and further cracked. Olefins that are of too low a carbon number are optionally modified by the process via a combination of ethylene oligomerization and oligomerization of light (C3-C7) olefins over a surface deactivated zeolite. The result is that light olefins can be incorporated into the desirable products of the process.

For example, ethylene can be oligomerized with any catalyst known to one skilled in the art into a distribution of linear even number alpha olefins. These olefins can be recycled into the process downstream of the thermal cracker, for example, so that a portion of the ethylene from the thermal cracker is converted to alpha olefins in the target range for the primary oligomerization step (C8-C14). The C4 and C6 alpha olefins from ethylene oligomerization can be recycled and combined with C3 to C7 olefins from the thermal cracker where they are oligomerized over a surface deactivated zeolite. The resulting product will contain internal olefins with a low degree of branching that after saturation (hydrotreating) will contain distillate and lube range components that can be combined with the oligomers from the primary oligomerization step. Optionally these products can be finished separately. The drilling fluid fraction may be distilled separately and used with internal olefins present or the entire stream may be hydrotreated and distilled with appropriate fractions used as fuels, solvents, or blended with PAO blend components from other oligomerization products. The heavy olefins from ethylene oligomerization can be saturated and recycled to a thermal cracker to make more olefins.

In a very limited embodiment ethanol, though not a paraffin, can be dehydrated to ethylene and converted to Group IV basestocks. The ethylene can be oligomerized to C4-C30 alpha olefins which can be further processed as described herein.

In a preferred embodiment, when waxy components are hydroisomerized to make Group III basestocks, the lighter iso-paraffinic byproducts from hydroisomerization are separated from feed to the thermal crackers so that the alpha olefins produced for oligomerization to Group IV basestocks are highly linear, thus improving the quality of the Group IV basestocks.

In a preferred embodiment, when using Fischer Tropsch feed material, at least two and preferably three or more thermal crackers are used to crack the paraffinic Fischer Tropsch syncrude products due to the broad carbon distribution. Such Fischer Tropsch products may optionally be hydrotreated to saturate olefins and/or alcohols resulting in a highly paraffinic feed to the thermal crackers. The Fischer Tropsch products may also be separated or distilled into cuts, such as C5-C9, C10-C15 and C16-C20. Such separation makes it possible to better control the operating conditions of the thermal crackers to optimize yield to olefin products, preferably linear alpha olefin products. These thermal crackers may be operated on a once through basis or may be operated at lower conversion with separation and recycle of the unreacted paraffinic products. Such recycle operation makes it possible to optimize the yield of higher olefin products which will enhance the quality and yield of the Group IV basestock products.

Renewable paraffin feeds resulting from the hydrodeoxygenation of triglycerides and fatty acids generally have a narrow carbon distribution making it easier to control thermal cracking in a single unit.

Thermal cracking of paraffin products from Fischer Tropsch syncrude and renewable feeds, such as hydrodeoxygenated triglycerides, results in production of a portion of the product as light olefins in the C2 to C7 range. These light olefins fall outside the target range for the primary oligomerization of approximately C8 to C14. The range C8 to C14 is used only as an example; within the process of the present invention this range can be adjusted according to the specific requirements to make high quality feedstock for oligomerization in the primary oligomerization reactor to Group IV basestock products over traditional oligomerization catalysts such as BF3 or AlCl3.

Therefore, it is an objective of the present invention to upgrade the light C2 to C7 olefins into the C8 to C14 range for feed to the primary oligomerization reactor or directly into useful products. Upgrading of light olefins may include dimerization, trimerization and/or oligomerization over the appropriate catalyst. Oligomerization of light olefins may include reaction with a surface deactivated zeolite catalyst such as ZSM-5, ZSM-11, ZSM-23 or ZSM-48, resulting in slightly branched internal olefins, a portion of which are in the diesel and lube oil range which, after hydrogenation and distillation, are useful as fuels and Group IV basestock products. A small portion of the C3-C7 olefins may also be converted to primary alcohols by hydroformylation and used as a co-catalyst in the primary oligomerization reactor.

The primary oligomerization reaction of the present invention for the higher olefin feed, may be carried out in a batch or continuous process in a fixed bed or stirred tank reactor or any other type of reactor known to one skilled in the art. Any oligomerization catalyst known to one skilled in the art may be used, including catalysts comprising BF3, AlCl3, Ziegler, Cr/SiO2, metallocene and the like.

The target olefin feed (C8-C14) to the primary oligomerization reactor may be distilled into narrow cuts and processed in campaigns or in parallel primary reactors. Commercial PAO that is currently in the market is made almost exclusively from 1-decene or in some cases may include some C8 and/or C12 olefin. All of these feeds are made by ethylene oligomerization. Since the proposed process produces olefins by thermal cracking of paraffins the resulting olefins have even and odd carbon numbers and a broad distribution. The broader distribution of the feed olefins may lead to a disadvantage in product properties. For example the Naock Volatility is an important property and can be strongly influenced by the carbon number distribution and distillation. When the broad range of olefins are used in the primary oligomerization reactor the product has all carbon numbers even and odd. If only 1-decene is used as feed the ologomerization products (dimer, trimer, tetramer etc.) is C20, C30, C40+. If the desired properties can be realized with a product in the C26 to C46 range anything lighter than C26 will contribute to increasing the Noack Volatility. With a product that only has C20, C30, C40+ the front distillation can be easily cut between C20 and C30 since there is such a large gap. This is good for Noack Volatility but if properties such as blending characteristics, Viscosity or VI are better with some distribution of molecular weight, the present invention will be of value. In the present process however with every carbon number present it will be difficult to distill between C25 and C26 for example so the Noack Volatility will be higher than commercial products made with 1-decene. By distilling the feed to the primary oligomerization reactor, we can still utilize the broader olefin feed distribution with even and odd carbon numbers and have sharp distillation cuts. For example, if the primary oligomerization feed is C8 to C14 we could distill into approximately 3 carbon number cuts such as C8-C10, C10-C12 and C12-C14. Distillation is not perfect and there will likely be some overlap of the cuts but assuming the cuts are made as outlined the resulting oligomerized products will have gaps between the dimers and trimers. For example, C8-C10 olefin feed has oligomers (dimers, trimers, tetramers+) from C16 to C40+. The + implies a small amount of pentamers and higher oligomers. With this feed there are no oligomers of carbon number C21, C22 and C23. Likewise, a C10-C12 olefin feed has oligomers of from C20 to C48+ with no oligomers between C25 and C29. The C12-C14 olefin feed has oligomers from C24 to C56+ with no oligomers between C29 and C35.

These breaks where no oligomers occur will make it possible to make sharper distillation cuts and control product properties such as Noack Volatility. The resulting PAO products can be blended together as desired or with other products including the lube fraction made herein by oligomerization of the light olefins over a surface deactivated zeolite. Distilled cuts may be combined to make products of the desired viscosity range with improved Noack Volatility compared to products made by oligomerization of the broad (C8-C14) range feedstock only.

Products of the higher olefins oligomerization reactor may be finished by hydrotreating and distillation. Such products may be blended together in any portion to make basestocks for a variety of applications. Optionally, products may be separated. For example, products from a renewable feed may be processed separately if desired. In a preferred embodiment, the process will produce both Group III and Group IV basestocks of predominantly low viscosities in the 2 to 10 cSt (at 100 C) range. The process will optionally also produce a smaller portion of higher viscosity, high VI, Group IV product (that can be used as a viscosity index VI improver) and/or an alkylated aromatic which can be used as a polar aprotic basestock or blending component.

The present invention makes it possible to convert paraffins, for example, from natural gas, coal or any carbonaceous feed via syn gas and Fischer Tropsch and/or from hydrodeoxygenated renewable feedstocks such as triglycerides and fatty acids into a mixture of products which can be blended to formulate a range of high quality fuels and synthetic lubricant products. The products of the present invention are advantaged to not be dependent on the limited supply of 1-decene.

Figures

The process can be described by referring to FIG. 1, which is a process flow diagram representing a preferred embodiment. A Fischer Tropsch reactor (1) can be any type of reactor known to one skilled in the art, such as fixed bed, fluidized bed, micro channel or slurry bubble column. The preferred catalyst is a non-shifting catalyst with a high alpha preferably higher than 0.9, more preferably higher than 0.92. Carbon numbers given in brackets [ ] are for discussion purpose and not meant to be limiting.

Unprocessed product is removed from the Fischer Tropsch reactor system (1) in two streams. First light Fischer Tropsch (FT) syncrude [C5-C20] is transferred to hydrotreater (3) via line (2). Hydrotreater (3) saturates FT olefins and alcohols resulting in a very linear paraffinic product stream (4). Stream (4) is fed to a distillation column (5). Second heavy FT syncrude (48) [C20-C100] is fed to vacuum distillation column (69). A lighter fraction [C20-C49] is removed overhead in column (69) and transferred to distillation column (5) via line (49). Heavy waxy components [C50-C100] are removed from the bottom of distillation column (69) and transferred via line (75) to a thermal cracker 4 (76). Cracked product from thermal cracker 4 is transferred via line (88) to a column (77). Columns, such as (77), may be separators, distillation columns, or strippers. Light olefins [C7-] are removed overhead from column (77). Higher olefins in the target range [C8-C14] are removed as a side draw and transferred to the primary oligomerization reactor feed line via line (79). Heavy cracked product (80) [C15+] may be recycled to thermal cracker 4 (76) via line (89) or recycled to feed hydrotreater (3) via line (90) or removed as a purge (91).

Light paraffinic hydrocarbons [C5-C9] are removed overhead from column (5) via line (6) and transferred to thermal cracker 1 (7). Cracked products are transferred via line (8) to column (9). The heavier mostly non-cracked [C8-C9] product is recycled from column (9) via line (10) to extinction. Light olefins mostly [C7-] are removed overhead from column (9) and transferred via line (11) to the light olefin processing section. Thermal cracker 2 (42) fed by stream (40) [C10-C15] and thermal cracker 3 (52) fed by stream (50) [C16-C20] operate like thermal cracker 1 (7) with one exception that columns (44) and (54) have side draws (45) and (55) respectively which transfer olefins of the target range [C8-C14] to the primary oligomerization feed line and therefore a detailed description is not necessary.

Upgrading Light Olefins

Light olefins [C2-C7] may be upgraded to higher olefins [C4+] or to products by several steps described herein. Light olefins [C7-] are collected from each of the thermal crackers and transferred to column (13) via line (12). Ethylene is removed overhead from column (13) and transferred via line (27) to an oligomerization reactor (28). Ethylene can be effectively oligomerized to even number linear alpha olefins in the [C4-C30+] range. These are the only even number olefins in the process as olefins produced by thermal cracking and surface deactivated zeolites are both even and odd number. Optionally, the ethylene can be reacted over a trimerization catalyst producing 1-hexene in high yield. The alpha olefin product produced by oligomerization reactor (28) is transferred via line (29) to column (30). Light olefins below the target set for primary oligomerization [C4 and C6], for example, are removed overhead and recycled to column (13) via line (36). Any unreacted ethylene, methane or other light gases are purged via line (17) and can be used as feedgas or fuel. Olefins in the target range [C8-C14] are transferred via line (31) and (58) to the primary oligomerization reactor (57). Olefins heavier than the target range [C16+] are transferred via line (37) to hydrotreater (3) where they are saturated and recycled into the process as paraffin feed for thermal cracking.

Light olefins, including [C3-C7] olefins removed via line (14), are subjected to oligomerization in a reactor (15) over a surface deactivated zeolite such as ZSM 5, ZSM-11, ZSM-23, or ZSM-48. The resulting product includes slightly branched internal olefins which are transferred by line (21) to column (22).

Product olefins [C8+] are slightly branched and after saturation can be used to make finished products. These products are transferred via line (68) to hydrotreater (61) where they can be blended with products from the primary oligomerization reactor and hydrotreated to saturate olefins and distilled into solvents, fuels and basestocks. Optionally these products can be campaigned through hydrotreating and distillation and stored as separate products. They can be sold separately or blended with PAO products from the primary oligomerization.

Optionally a slipstream (16) of light olefins can be fed to hydroformylation reactor (18) with carbon monoxide and hydrogen (20) to produce a mixed alcohol stream (19) that can be used as a co-catalyst in reactor (57).

Optional Blendstock Production

Optionally, some of the alpha olefin product of line (31) can be transferred via line (32) to oligomerization reactor (33) to make a high VI viscosity improver product (34). Oligomerization reactor (33) can use any oligomerization catalyst known to one skilled in the art, but preferably uses a chromium on silica catalyst. Another option of the process is to produce an aprotic blendstock using slightly branched olefins (23) which are transferred via line (24) to alkylation reactor (26). Aromatic feed is imported via line (25). The alkylated aromatic product (35) can be blended with the lube basestocks of the present invention.

Production of Group IV Basestocks

Figure 4:
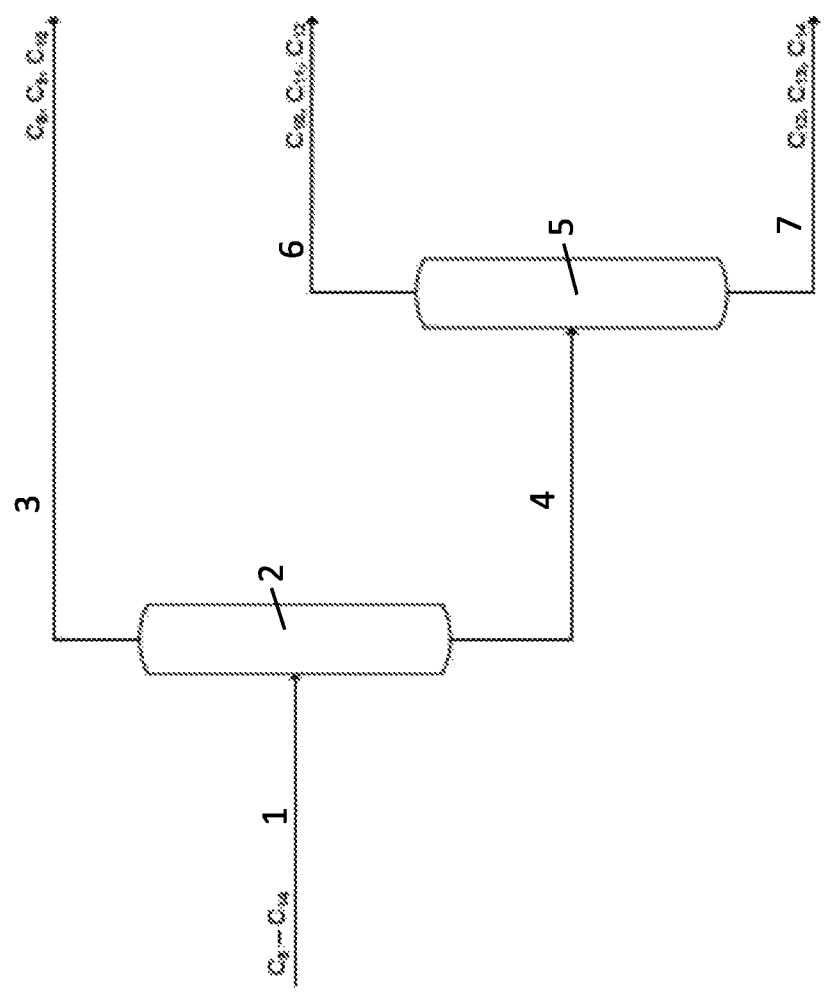
FIG. 4 is a simplified process flow diagram of a preferred embodiment of a segment of the process of the present invention.

Alpha olefins from thermal cracking that are in the target carbon number range [C8-C14], for example, are transferred to oligomerization reactor (57) feed line via lines (45), (55) and (79) where they are mixed with alpha olefins from light olefin upgrading (58) and optionally mixed alcohol co-catalyst (19). The mixed alcohol stream could be added to the feed line or directly into the reactor as known to one skilled in the art. The mixed alpha olefin feed is transferred to oligomerization reactor (57) via line (56). Optionally this feed stream can be distilled into narrow cuts as shown in FIG. 4. These cuts can be campaigned through reactor (57) or several parallel reactors can be used. Reactor (57) can use any catalyst known to one skilled in the art, but preferably uses a catalyst comprising boron trifluoride BF3. The resulting oligomers (59) are mixed with the product (68) from column (22) and optionally hydroisomerized product (72) and transferred to hydrotreater (61) via line (60). Hydrotreated product is transferred to column (63) via line (62) where it is separated into solvents and/or fuels which are removed via line (64) and various cuts of synthetic lubricant basestocks of different viscosities, such as 2 cSt removed via line (65), 4 cSt removed via line (66) and 6 cSt (67). These cuts may be varied to meet market requirements. The final product workup including hydrotreating and distillation may include other steps such as water wash, separation, filtration etc. There may be multiple distillation columns as is known to one skilled in the art. The main product streams 59, 68, and 72 may be co-processed in the final workup or processed separately.

Production of Group III Basestocks

Heavy waxy product exits the bottom of column (5) and is transferred to hydroisomerization reactor (71) via line (70). Hydroisomerization reactor (71) may include one or two stages or any configuration known to one skilled in the art and may use any hydroisomerization catalyst known to one skilled in the art. Hydroisomerized product is transferred to hydrotreater (61) via line (72) where it may be co-processed with Group IV basestock in line (60) or it may be campaigned through the hydrotreater (61) and distillation (63), producing a range of solvents and basestock products of different viscosities similar to the Group IV basestock products.

Optional Renewable Feedstock

Optionally, a clean degummed feedstock comprising materials selected form the group comprising triglycerides, diglycerides, monoglycerides, and/or free fatty acids (81) is fed to hydrodeoxygenation reactor (82) where it is converted in high yield to linear paraffins predominately [C10-C22]. Intermediate paraffin product is transferred to column (85) via line (83) where light products, including light hydrocarbons (predominately propane), water, and carbon dioxide, are removed overhead (84). This propane product may optionally be dehydrogenated to propylene which can be added to the feed to the surface deactivated zeolite reactor (15). Any unreacted product is removed from the bottom of column (85) and recycled to hydrodeoxygenation reactor (82) via line (87). Paraffin product (86), predominately [C10-C22], are transferred to thermal cracker 3 (52) where it is processed with a paraffin fraction from column (5) of similar carbon distribution. The system as described will result in this portion of the finished Group IV basestocks produced being renewable.

Figure 2:
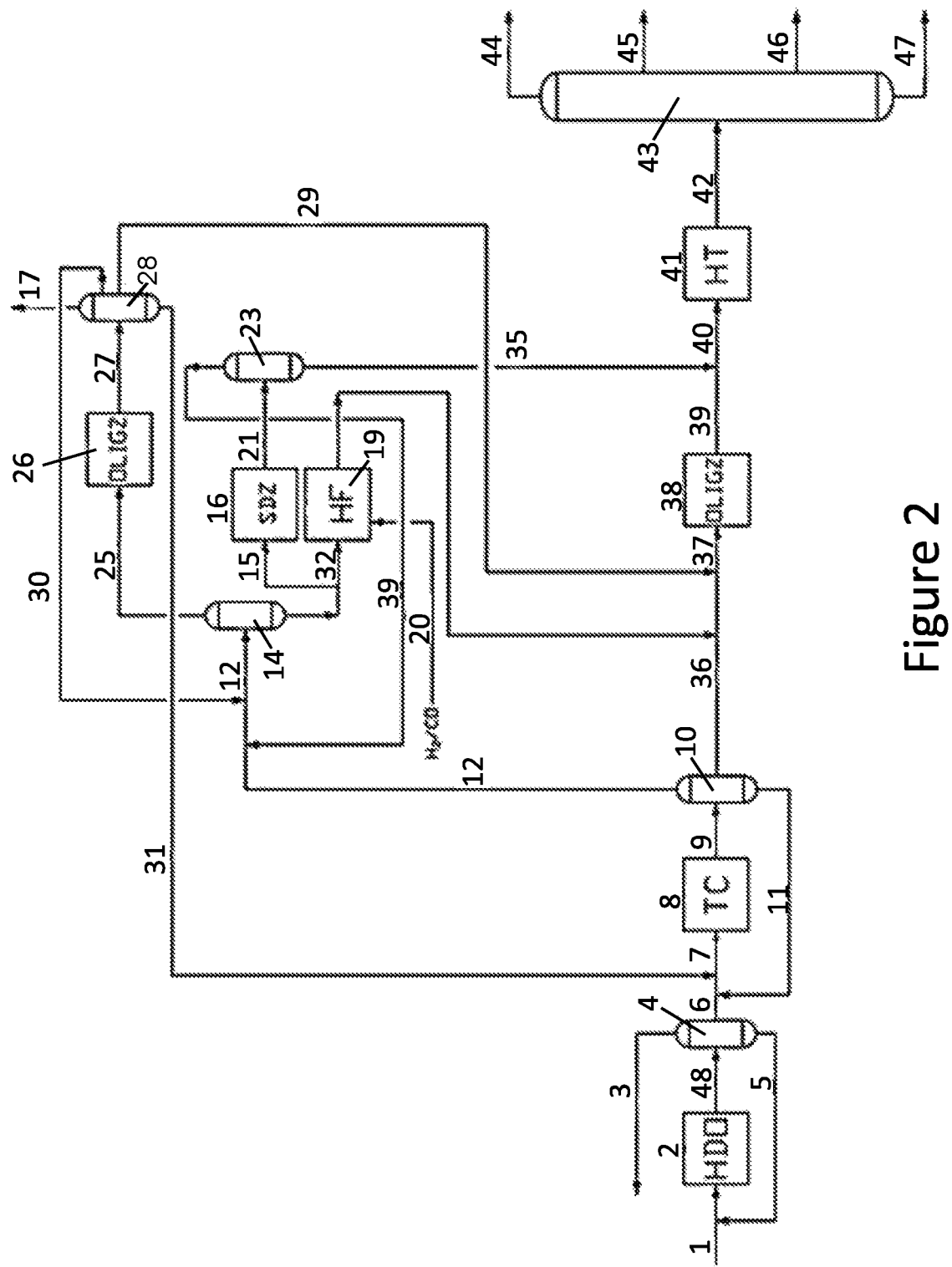
FIG. 2 is a simplified process flow/diagram of a second preferred embodiment of the present invention.

FIG. 2 represents another, second preferred embodiment of the present invention. Clean degummed renewable feedstock selected from the group comprising triglycerides, diglycerides, monoglycerides, and free fatty acids (1) is fed to a hydrodeoxygenation unit (2). Hydrodeoxygenated product is transferred via a line (48) to a column (4) where light products, including light hydrocarbons (predominately propane), water, and carbon dioxide, are removed overhead (3). The propane may optionally be dehydrogenated to propylene and added to the feed to the surface deactivated zeolite reactor (16). Heavy un-reacted product is removed from the bottom of column (4) and recycled to hydrodeoxygenation unit (2) via line (5). Paraffin products, predominately [C10-C22], are transferred to thermal cracker (8) via lines (6) including recycle streams (11) and (31). Cracked product from the thermal cracker (8) is transferred via line (9) to a column (10). Column (10) may alternately be a distillation column or stripper. Light olefins (12) [C7-] are removed overhead from (10) for further processing. Higher olefins in the target range [C8-C14] are removed as a side draw and transferred to the primary oligomerization reactor via a feed line (36). Heavy un-cracked product [C15+] may be recycled to thermal cracker (8) via line (11). This stream (11) may optionally be saturated if desired.

Light olefins [C2-C7] are upgraded to higher olefins and useful products by several steps described herein. Light olefins are collected from the thermal cracker and transferred via line (12) where they are joined with recycle streams (30) and (39) and finally via line (12) to column (14). Ethylene is removed overhead from column (14) and transferred via line (25) to oligomerization reactor (26). Ethylene can be effectively oligomerized to even number linear alpha olefins in the [C4-C30+] range. Optionally, the ethylene can be reacted over a trimerization catalyst producing 1-hexene in high yield. The alpha olefin product produced by oligomerization reactor (26) is transferred via line (27) to a column (28). Light gases [C2-] are purged via line (17). Light olefins below the target set for higher olefins [C4-C6], for example, are removed from the column (28) and recycled to column (14) via line (30). The remaining light olefins, including [C3-C7] olefins, are transferred via line (15) to reactor (16) and subjected to oligomerization over a surface deactivated zeolite, such as ZSM5 ZSM-11, ZSM-23 or ZSM-48. The oligomerized product includes slightly branched internal olefins which are transferred via line (21) to column (23). Light un-reacted olefins [C3-C7] are recycled via line (39). Product olefins are transferred via line (35) for finishing in hydrotreater (41) and distilled in column (43). Optionally a slipstream of light olefins (32) from stream (15) can be transferred to hydroformylation reactor (19) and reacted with syngas stream (20) to make a mixed stream of alcohols that can be used as co-catalyst in oligomerization reactor (38). The co-catalyst alcohol mix may be added to the feed stream of olefins (37) or directly into the reactor or by any method known to one skilled in the art. Alpha olefins from thermal cracking that are in the target carbon number range [C8-C14], for example, are transferred to oligomerization reactor (38) via line (36) where they are mixed with alpha olefins from light olefin upgrading (29). The mixed alpha olefin feed is transferred to oligomerization reactor (38) via line (37). The mixed olefin feed comprising [C8 to C14] olefins may optionally be distilled into narrow cuts as shown in FIG. 4. These cuts can be campaigned through reactor (38) or can be run through separate parallel reactors and distillation systems. The products can be blended as needed to make finished fuels, solvents and lube basestocks. Processing in this manner makes it possible to better control properties such as Noack Volatility in the finished products. Reactor (38) can use any catalyst known to one skilled in the art but preferably uses a catalyst comprising BF3. The resulting oligomers removed via line (39) are mixed with the product (35) from column (23) and transferred to hydrotreater (41) via line (40). Hydrotreated product is transferred to column (43) via line (42) where it is separated into fuels and solvents (44) and various cuts of different viscosities, such as 2 cSt (45), 4 cSt (46) and 6 cSt (47). These cuts may be varied to meet market requirements.

Figure 3:
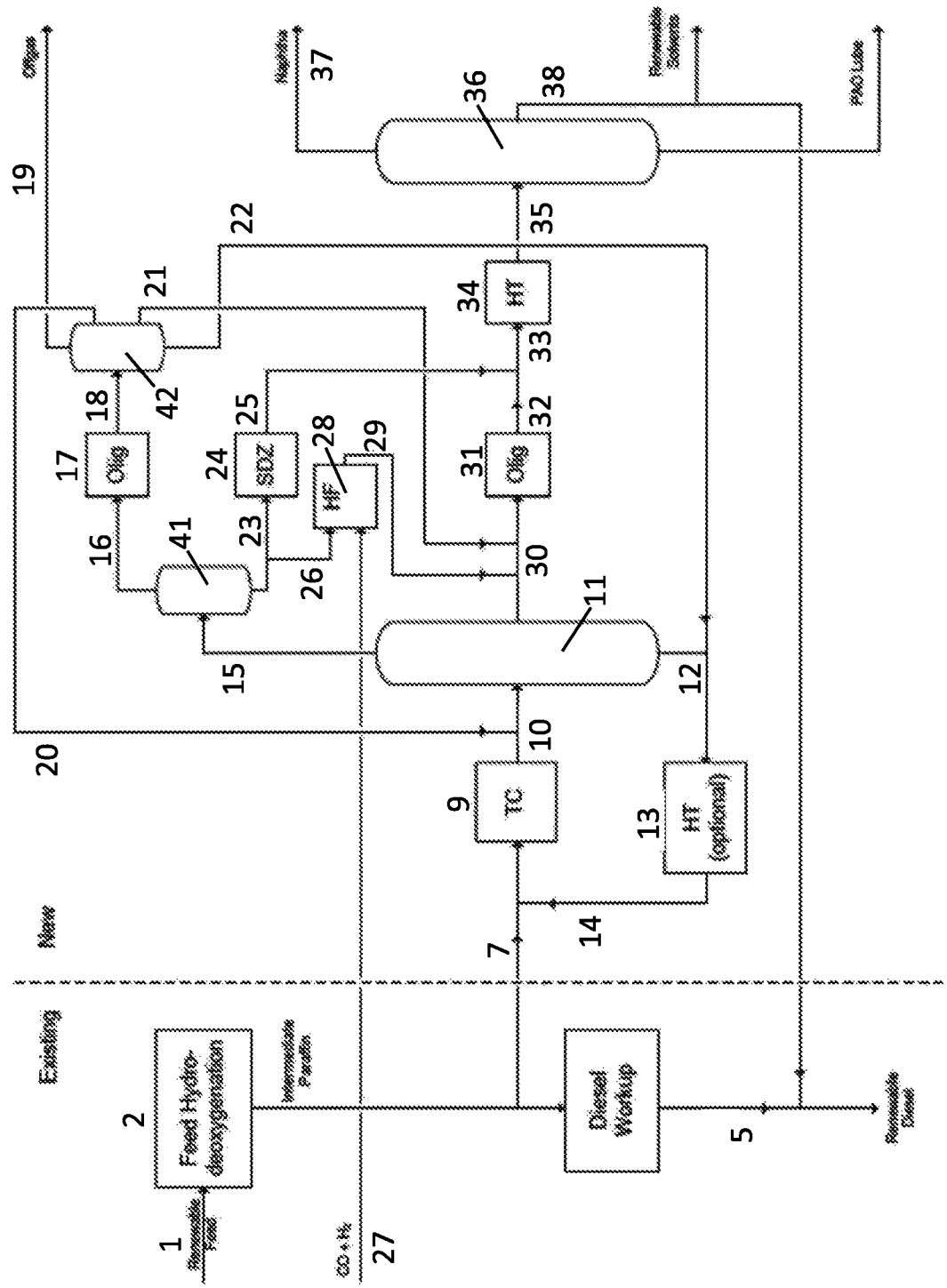
FIG. 3 is a simplified process flow diagram of a third preferred embodiment of the present invention.

FIG. 3 is another preferred embodiment of the present invention. FIG. 3 depicts a process that consists of an existing renewable diesel facility with a new poly-alpha-olefin (PAO) production facility that uses an intermediate paraffin product from the renewable diesel facility as a feedstock. An existing renewable diesel facility will have downstream workup or refining steps comprising hydroisomerization. This hydroisomerization can be greatly reduced or eliminated as the product of the surface deactivated zeolite reactor (24) has adequate branching, therefore reducing or eliminating the need for the hydroisomerization step depending on how much renewable diesel is made. The same configuration could be a new stand-alone facility that produces both renewable diesel and PAO products with flexibility with respect to how much renewable diesel is made. Renewable feed (1) is introduced to a feed hydrodeoxygenation unit (2) where triglycerides and/or free fatty acids are hydrodeoxygenated to produce products comprising [C10 to C22] paraffins and light gases, including propane, water, CO and CO2. The propane product produced in the hydrodeoxygenation reaction may optionally be dehydrogenated to propylene and added to the feed of the surface deactivated zeolite reactor (24). The paraffin products are separated from the light gases and split (in a limited embodiment the split may include 100% of the paraffin feed going to the PAO process) for use as renewable diesel feed or as feed (7) to the PAO process where they are combined with recycled paraffin product (14) and fed to a thermal cracker (9). Recycled paraffin product (12) is optionally hydrotreated (13) to saturate any olefins.

Thermal cracked product (10) including light olefins and un-cracked paraffins is transferred to a distillation column (11) where light and intermediate olefins are separated from un-reacted paraffins. Light olefins [C2-C7] are removed and transferred via line (15) to column (41) where they are separated into ethylene (16) and [C3-C7] olefins (23). Ethylene (16) is oligomerized to higher even number linear alpha olefins in reactor (17). The olefin product is transferred to column (42) via line (18) where it is separated into light gases (19), [C4-C6] olefins (20), [C8-C14] olefins (21) and heavy olefins (22). The heavy olefin stream is combined with recycle stream (12) and saturated in hydrotreater (13). Light olefins [C3-C7] are transferred via line (23) to surface deactivated zeolite reactor (24) where they are oligomerized into product range internal olefins that are transferred via line (25) to combine with products from the primary oligomerization reactor (32). A slipstream of light olefins from stream (23) is transferred via line (26) to combine with syngas feed stream (27) and fed into hydroformylation reactor (28) to make a mixed alcohol stream (29) that will be used as a co-catalyst in primary oligomerization reactor (31). Target range olefins [C8-C14] are removed from column (11) and transferred via line (30) to the primary oligomerization reactor (31) where they react with olefin stream (21) and alcohol co-catalyst (29). Oligomerization product (32) is combined with oligomerization product (25) and transferred via line (33) to hydrotreater reactor (34). The hydrotreated product (35) is transferred to column (36) where it is separated into products such as naphtha (37), renewable solvents/diesel (38), and renewable lube cuts as required. The renewable diesel cut from column (36) can be added to renewable diesel (5). Optionally, the oligomers from the surface deactivated zeolite may be processed independently. The products may be kept separate or blended as desired.

FIG. 4 is an example of how a complex mixed olefin feed with even and odd carbon number olefins can be advantageously processed. Mixed olefin stream (1) comprising [C8 to C14] olefins inclusive of all even and odd numbers is transferred to column (2) where it is distilled into a product comprising predominantly [C8, C9 and C10] (3) and a bottoms fraction comprising [C10] and heavier components (4). There is some small amount of overlap in the products. Bottoms fraction (4) is fed to a second distillation column (5) where it is distilled into two products. Overhead product (6) comprising predominantly [C10, C11 and C12] and bottoms product (7) comprising predominantly [C12, C13 and C14]. Narrow cut olefin products (3), (6) and (7) can be processed advantageously to enhance the final product properties. For example, when oligomerized with a BF3 catalyst and alcohol co-catalyst the products are mainly dimers, trimers and tetramers with a small amount of pentamers and heavier oligomers. By processing a narrow cut there is a gap between the largest dimer and the shortest trimer for each cut. For example, for the three cuts described above the oligomers and gaps are specified below.

| Feed olefin | largest dimer | shortest trimer | oligomers not produced (gap) |
|---|---|---|---|
| Cut 1 C8,C9,C10 | C20 | C24 | C21,C22,C23 |
| Cut 2 C10,C11,C12 | C24 | C30 | C25,C26,C27,C28,C29 |
| Cut 3 C12,C13,C14 | C28 | C36 | C29,C30,C31,C32,C33,C34 C35 |

These products can be easily distilled into sharp cuts between the dimer/trimer gap. This would not be possible when processing the full olefin feed of [C8 to C14]. These sharp cuts can be blended to make better quality products with improved Noack Volatility.

The present invention makes it possible to convert paraffin feeds, and in a very limited embodiment, ethanol into a range of olefins from [C2 to C30] or greater and oligomerizing those olefins to make solvents, distillates, and PAO basestock products.

Whereas, the present invention has been described in relation to the drawings attached hereto, it should be understood that other and further modifications, apart from those shown or suggested herein, may be made within the spirit and scope of this invention.

What is claimed is:

1. A process to produce solvents, fuels, and poly-alpha-olefin (PAO) basestocks from a paraffin feed comprising the steps of:
    (a) thermally cracking a paraffin feed stream to produce even and odd carbon number C3 to C30+ alpha olefins;
    (b) oligomerizing ethylene produced in step (a) to make even number C4 to C30+ alpha olefins;
    (c) oligomerizing C3 to C7 alpha olefins produced in step (a) over a surface deactivated zeolite catalyst to make branched internal olefins;
    (d) combining C8 to C14 alpha olefins from step (a) and C8 to C14 even number alpha olefins from step (b) to produce a combined product, and distilling the combined product to produce a first cut comprising C8 to C10 alpha olefins, a second cut comprising C10 to C12 alpha olefins, and a third cut comprising C12 to C14 alpha;
    (e) oligomerizing each cut from step (d) individually to produce a PAO blend product from each cut;
    (f) distilling each PAO blend product from step (e) individually into (1) dimers and (2) trimers and heavier components;
    (g) blending the trimers and heavier components from step (f) in any combination to make PAO products;
    (h) hydrotreating and distilling the branched internal olefins of step (c) into solvents, drilling fluid, distillates, and/or PAO products; and
    (i) blending PAO products of step (h) with the products of step (g).

2. The process as set forth in claim 1 further comprising hydrotreating the cuts of step (f) or the PAO products of step (g).

3. The process as set forth in claim 1 where the oligomerizing of step (b) is trimerizing.

4. The process as set forth in claim 1 wherein the paraffin feed is a Fischer Tropsch product fraction.

5. The process as set forth in claim 1 wherein the paraffin feed is a hydrodeoxygenated fat or oil comprising triglycerides, mono or diglycerides, and/or free fatty acids.

6. The process as set forth in claim 5 wherein propane produced by hydrodeoxygenation of the feed stream is dehydrogenated to propylene which can be used in step (c).

7. The process as set forth in claim 1 wherein the PAO products of step (g), step (h), and/or step (i) have improved Noack volatility.

8. The process of claim 1 further comprising using a slipstream of an olefin fraction from the process to alkylate an imported aromatic feedstock to make a polar aprotic blendstock useful for blending with products produced by the process.

9. The process of claim 1 further comprising sending a slipstream of C3 to C7 olefins produced in the process to a hydroformylation reactor to produce a viscosity index improver.

10. The process of claim 1 further comprising hydroisomerizing a paraffin fraction produced by the process to make group III basestocks, solvents, distillates, or drilling fluids, wherein the paraffin fraction is not a paraffin fraction used as feed to a thermal cracker.

11. The process of claim 1 further comprising separating one or more products comprising branched internal olefins from step (c).

12. The process of claim 1 wherein step (a) comprises at least one thermal cracker, where the at least one thermal cracker is operated with a limited conversion per pass and heavy un-cracked product is recycled.

13. The process of claim 1 wherein the oligomerization catalyst in step (e) is $BF_3$, $AlCl_3$, Ziegler, $Cr/SiO_2$, or metallocene.

14. The process of claim 1 wherein the catalyst in step (c) is ZSM-5, ZSM-11, ZSM-23, or ZSM-48.

15. The process of claim 1 wherein a portion of the C3 to C7 alpha olefins produced in step (a) are converted to primary alcohols by hydroformylation and used in step (e) as a co-catalyst.

16. The process of claim 1 wherein step (e) further comprises an oligomerization reactor, where the oligomerization reactor of step (e) is a batch or continuous reactor and also a fixed bed or stirred tank reactor.

17. The process of claim 1 wherein the paraffin feed stream of step (a) is an intermediate paraffin product of an existing renewable diesel plant.

18. A process to produce solvents, distillates, drilling fluids, and PAO basestocks comprising:
(a) dehydrating ethanol to ethylene;
(b) oligomerizing the ethylene of step (a) to produce C4 to C30+ alpha olefins;
(c) oligomerizing C4 to C6 olefins from step (b) over a surface deactivated zeolite to make branched internal olefins;
(d) distilling C8 to C14 even number alpha olefins from step (b) into a first cut comprising C8 and C10 alpha olefins, a second cut comprising C10 and C12 alpha olefins, and a third cut comprising C12 and C14 alpha olefins;
(e) oligomerizing each cut from step (d) individually to produce a PAO blend product from each cut;
(f) distilling each PAO blend product from step (e) individually into (1) dimers and (2) trimers and heavier components;
(g) blending the trimers and heavier components from step (f) in any combination to make PAO products;
(h) hydrotreating and distilling the branched internal olefins of step (c) into solvents, drilling fluid, distillates, and/or PAO products; and
(i) blending PAO products of step (h) with the products of step (g).

19. The process of claim 18 further comprising hydrotreating the cuts of step (f) or the PAO products of step (g).

20. The process of claim 18 further comprising hydrotreating the olefins of step (b) that are heavier then C16 and using them as feed to a thermal cracker to make more alpha olefins, a portion of which may be separated and recycled to the process.

21. The process of claim 18 further comprising distilling a fraction of the product of step (c) into one or more products comprising branched internal olefins.

22. The process of claim 18 wherein the oligomerization catalyst in step (e) is $BF_3$, $AlCl_3$, Ziegler, $Cr/SiO_2$, or metallocene.

23. The process of claim 18 wherein the catalyst in step (c) is ZSM-5, ZSM-11, ZSM-23, or ZSM-48.

24. The process of claim 18 wherein a portion of the C4 and C6 olefins produced step (b) are converted to primary alcohols by hydroformylation and used in step (e) as a co-catalyst.

25. The process of claim 18 wherein step (e) further comprises an oligomerization reactor, where the oligomerization reactor of step (e) is a batch or continuous reactor and also a fixed bed or stirred tank reactor.

* * * * *